(12) United States Patent
Tao et al.

(10) Patent No.: US 12,144,936 B2
(45) Date of Patent: Nov. 19, 2024

(54) DOUBLE THERMOFORM CANNULA

(71) Applicant: ABIOMED, Inc., Danvers, MA (US)

(72) Inventors: Zhenghong Tao, Danvers, MA (US); Stephen Vaughan, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 1016 days.

(21) Appl. No.: 16/912,293

(22) Filed: Jun. 25, 2020

(65) Prior Publication Data
US 2020/0406001 A1    Dec. 31, 2020

Related U.S. Application Data

(60) Provisional application No. 62/868,476, filed on Jun. 28, 2019.

(51) Int. Cl.
*A61M 25/00* (2006.01)
*A61M 25/01* (2006.01)
(Continued)

(52) U.S. Cl.
CPC ...... *A61M 25/005* (2013.01); *A61M 25/0012* (2013.01); *A61M 25/0021* (2013.01); *A61M 25/0045* (2013.01); *A61M 25/0054* (2013.01); *A61M 25/0158* (2013.01); *A61M 60/13* (2021.01); *A61M 60/148* (2021.01);
(Continued)

(58) Field of Classification Search
CPC ............ A61M 25/005; A61M 25/0012; A61M 25/0021; A61M 25/0045; A61M 25/0158; A61M 60/13; A61M 60/148; A61M 60/216; A61M 60/414; A61M 60/422;
(Continued)

(56) References Cited

U.S. PATENT DOCUMENTS 5,441,489 A * 8/1995 Utsumi ............. A61M 25/0054
604/525
5,545,151 A * 8/1996 O'Connor ......... A61M 25/0045
604/524
(Continued)

FOREIGN PATENT DOCUMENTS

CN    107735144 A    2/2018
EP    3437668 A1    2/2019
(Continued)

OTHER PUBLICATIONS

International Search Report and Written Opinion for International Application No. PCT/US2020/039640 dated Oct. 12, 2020 (10 pages).

(Continued)

*Primary Examiner* — Nathan R Price
*Assistant Examiner* — John A Doubrava
(74) *Attorney, Agent, or Firm* — Botos Churchill IP Law LLP

(57) ABSTRACT

Systems and methods for providing a reinforced cannula for use in a blood pump assembly. The reinforced cannula comprises one or more thermoformed reinforced end portions. The thermoformed reinforced end portions may be stiffer than a medial portion of the cannula, allowing the medial portion of the cannula body to stretch and bend more readily than the cannula ends when the cannula is subject to an applied stress, reducing the stress and strain on the cannula ends.

17 Claims, 3 Drawing Sheets

(51) Int. Cl.
  *A61M 60/13*    (2021.01)
  *A61M 60/148*   (2021.01)
  *A61M 60/174*   (2021.01)
  *A61M 60/216*   (2021.01)
  *A61M 60/414*   (2021.01)
  *A61M 60/422*   (2021.01)
  *A61M 60/585*   (2021.01)
  *A61M 60/857*   (2021.01)

(52) U.S. Cl.
  CPC ........ *A61M 60/174* (2021.01); *A61M 60/216* (2021.01); *A61M 60/414* (2021.01); *A61M 60/422* (2021.01); *A61M 60/585* (2021.01); *A61M 60/857* (2021.01); *A61M 2025/0042* (2013.01); *A61M 2207/10* (2013.01); *A61M 2210/125* (2013.01)

(58) Field of Classification Search
  CPC .............. A61M 60/585; A61M 60/857; A61M 2025/0042; A61M 2025/0098
  See application file for complete search history.

(56) References Cited

U.S. PATENT DOCUMENTS

| | | | |
|---|---|---|---|
| 6,295,877 | B1 | 10/2001 | Aboul-Hosn et al. |
| 8,795,576 | B2 | 8/2014 | Tao et al. |
| 2001/0010247 | A1* | 8/2001 | Snow ................ A61M 25/0041 156/171 |
| 2003/0158574 | A1* | 8/2003 | Esch ........................ A61F 2/013 606/200 |
| 2006/0106351 | A1* | 5/2006 | Lareau .................. B29C 48/335 264/176.1 |
| 2012/0197217 | A1 | 8/2012 | Coldren |
| 2015/0328382 | A1* | 11/2015 | Corbett ............... A61M 60/865 600/16 |
| 2015/0360003 | A1* | 12/2015 | Khalaj ............. A61M 25/0606 604/93.01 |
| 2017/0215918 | A1* | 8/2017 | Tao ..................... A61M 60/135 |
| 2018/0264183 | A1 | 9/2018 | Jahangir |
| 2019/0046702 | A1 | 2/2019 | Siess et al. |

FOREIGN PATENT DOCUMENTS

| | | |
|---|---|---|
| JP | 2013198633 A | 10/2013 |
| JP | 2017515581 A | 6/2017 |
| JP | 2019506938 A | 3/2019 |
| TW | 201216940 A | 5/2012 |
| WO | 2015175718 A1 | 11/2015 |
| WO | 2018234454 A1 | 12/2018 |

OTHER PUBLICATIONS

U.S. Appl. No. 16/625,491 (not yet published), filed Dec. 20, 2019.
Office action dated Mar. 1, 2024 for Japanese Application. No. 2021-577312, 11pp.).
Office Action from corresponding Indian Patent Application No. 202217002839 dated Apr. 22, 2024 (7 pp.).
Office Action issued in corresponding Israeli Patent Application No. 289206, mailed Aug. 5, 2024, 4 pages.

* cited by examiner

DOUBLE THERMOFORM CANNULA

CROSS-REFERENCE TO RELATED APPLICATIONS

This application claims priority from U.S. Patent Application No. 62/868,476 filed Jun. 28, 2019, which is incorporated by reference herein in its entirety. In addition, this application is related to U.S. Patent Publication No. 2017/0215918 A1, entitled "Thermoform Cannula with Variable Cannula Body Stiffness," and U.S. Pat. No. 8,795,576 B2, entitled "Radiopaque Cannula Marker," both of which are hereby incorporated by reference in their entirety.

BACKGROUND

An intravascular blood pump assembly, such as an assembly with an intracardiac blood pump, may be introduced into the heart to deliver blood from the heart into an artery. Intravascular blood pumps can be introduced percutaneously during a cardiac procedure through the vascular system, such as by a catheterization procedure. Some blood pumps are designed to support the left side of the heart, where they pull blood from the left ventricle of the heart and expel the blood through a cannula into the aorta. Some blood pumps that support the left side of the heart are introduced by a catheterization procedure through the femoral artery, into the ascending aorta, across the aortic valve, and into the left ventricle. Some systems are designed to support the right side of the heart, where the blood pump is introduced through a vein and into the right side of the heart through the venous system (e.g., the vena cava). Blood pump systems may also be surgically implanted or inserted through the subclavian and/or carotid arteries. During the insertion of a blood pump assembly into a patient through a blood vessel, it may be difficult to advance the blood pump through the tortuous paths or calcified anatomy of the patient.

Complications involving the introduction of the pump due to these tortuous paths may, in some cases, cause damage to the blood pump assembly, or to the patient. For example, in right heart procedures, damage may occur as the blood pump navigates the tortuous path toward and in the right heart (e.g. spanning between the inferior vena cava and the pulmonary artery). In some instances, the cannula of the blood pump bears the majority of the load exerted on the pump as it navigates the path toward and in the heart. For example, the cannula of a right heart blood pump may be stretched or bent as a result of its positioning. Similarly, the various interfaces between the cannula and the pump's inflow and outflow components may be stretched or bent, causing damage to the blood pump. Known blood pump assemblies include the Impella® pumps by Abiomed, Inc. The Impella® pump systems generally include a catheter, a pump, a power source to drive the rotor of the pump, a cannula for crossing a heart valve, and an atraumatic extension. Impella® pumps may be introduced into a patient to support the left heart or the right heart.

SUMMARY

The systems, methods, and devices described herein provide a reinforced cannula for use in a blood pump assembly, configured to withstand the forces experienced during blood pump insertion and operation. In some aspects of the technology, the reinforced cannula is a double thermoform cannula with at least one thermoformed reinforced end portion that is stiffer than a medial portion of the cannula. The thermoformed outer end reinforcement layers cause the cannula body, rather than the cannula ends, to stretch more readily when the cannula is subject to an applied stress, thereby reducing the stress on the interfaces between the cannula ends and their respective adjacent components. Thus, the thermoformed reinforced end portions, also referred to as the thermoformed outer end reinforcement layers, may serve as strain relief sections for the cannula.

A thermoformed outer end reinforcement layer may be located at an interface between the cannula and one of the other components of the blood pump assembly. For example, a thermoformed outer end reinforcement layer may be located at the interface between the distal end of the cannula and distal components (e.g., a blood inflow cage) or between the proximal end of the cannula and the pump housing, or both. A thermoformed outer end reinforcement layer may help prevent the separation of the cannula from the other components of the blood pump assembly. Thermoformed outer end reinforcement layers may also improve the strength at the interface between the cannula and the other components (e.g. a blood inflow cage positioned distally of the cannula).

The thermoformed outer end reinforcement layer may have a higher durometer hardness than a medial portion of the cannula's outer layer. In some implementations, the thermoformed outer end reinforcement layer is at least two times as stiff as the medial portion of the cannula. In other implementations, the thermoformed outer end reinforcement layer is between about 1.5 times and 5.5 times as stiff as the medial portion of the cannula. In some implementations, the thermoformed outer end reinforcement layer is between about 2 times and about 5 times as stiff as the medial portion of the cannula. In further implementations, the thermoformed outer end reinforcement layer is between about 3 times and about 4 times as stiff as the medial portion of the cannula. In certain implementations, the thermoformed outer end reinforcement layer is about 3.5 times as stiff as the medial portion of the cannula.

Additionally, one or more layers of the cannula body may also be formed using a thermoforming process. The incorporation of the thermoformed layers into the medial portion of the cannula may provide additional structural reinforcement to the cannula along its length. Further, the thermoforming of the one or more layers of the cannula body may serve to increase the manufacturing yield for cannulas of pumps with short bonding areas.

According to some aspects of the technology, an intravascular blood pump system for insertion into the heart includes a pump with a rotor and one or more blades positioned within a pump housing, for conveying fluid through the pump housing. A drive system is also included with a motor and a drive line. The motor may be an onboard motor powered by an electrical line or an external motor with a drive cable connecting the pump and motor. The blood pump system further has an elongate catheter that connects the pump to the external control system outside the patient and through which the drive cable or electrical line would run. A cannula is positioned distal of the pump housing and interfaces with the distal end of the pump housing. As used herein, "distal" refers to a direction pointing away from an operator of the blood pump, and toward the patient. Likewise, "proximal" refers to a direction pointing toward an operator of the blood pump, and away from the patient. The cannula has a length, a proximal end, a medial portion, and a distal end. The distal end of the cannula is attached to the proximal end of an inflow cage extending distally from the cannula; the distal end of the inflow cage is attached to a distal atraumatic projection. The inflow cage spaces apart the cannula and the distal atraumatic projection, and blood flows past the inflow cage to enter the cannula.

The cannula may be configured with at least three concentric cylindrical layers: an inner layer, a reinforcement layer, and an outer layer. The layers extend longitudinally along the length of the cannula and define the body of the cannula from the distal end of the cannula to the proximal end of the cannula. The outer layer surrounds the reinforcement layer, which surrounds the inner layer. The three concentric layers, the inner layer in particular, further define a lumen that extends along the length of the cannula. The inner and outer layer of the cannula body may be thermoformed. In certain implementations, a thermoformed outer end reinforcement layer is placed over the outer layer of the cannula at least one of the distal end and the proximal end of the cannula. The combination of the thermoformed outer end reinforcement layer and the thermoformed inner and outer layers lends structural stability to the cannula body, and allows the thermoformed end reinforcement layers—rather than the layers of the cannula body—to serve as strain relief sections of the cannula when the cannula is subject to shear forces during the insertion and operation of the cannula into the vasculature of a patient.

In some implementations, the cannula is configured with a thermoformed inner layer extending along the cannula's length. The inner layer comprises an inner material and has an inner diameter and an outer diameter. In some implementations, the outer diameter of the inner layer is between about 1 Fr and 5 Fr. In other implementations, the outer diameter of the inner layer is between about 2 Fr and 4 Fr. In certain implementations, the outer diameter of the inner layer is about 3 Fr. In certain implementations, the radial thickness of the inner layer is between about 0 mm and about 0.2 mm. In further implementations, the radial thickness of the inner layer is between about 0.05 mm and about 0.15 mm. In some implementations, the radial thickness of the inner layer is about 0.1 mm. In further implementations, the outer layer has a radial thickness between about 0 mm and about 0.15 mm. In certain implementations, the outer layer has a radial thickness between about 0.075 mm and about 0.125 mm. In certain implementations, the outer layer has a radial thickness of about 0.1 mm. The thicknesses of the respective layers can be adjusted to yield a given total thickness of the cannula. In certain implementations, the total radial thickness of the cannula is between about 0 mm and about 0.5 mm. In some implementations, the total radial thickness of the cannula is between about 0.15 mm and about 0.35 mm. In further implementations, the total radial thickness of the cannula is about 0.3 mm. In some implementations, the outer diameter of the medial portion of the cannula is between about 17 Fr and about 22 Fr. In certain implementations, the outer diameter of the medial portion of the cannula is between about 18 Fr and about 21 Fr. In further implementations, the outer diameter of the medial portion of the cannula is about 19.5 Fr.

For a cannula having an outer layer with a fixed outer diameter, the amount of material at a given longitudinal point along the length of the cannula can be adjusted by adjusting the radial thickness (e.g., the outer diameter and/or the inner diameter) of the inner layer during the manufacturing process. Adjusting the amount of material that is present at a longitudinal point along the length of the cannula changes the stiffness of that point, with points having more material being stiffer and points having less material being less stiff. Thus, in order to create a desired stiffness profile along the length of the cannula, the radial thickness of the inner layer can be adjusted such that a given point along the length of the cannula has an amount of material with a desired stiffness.

Additionally, the cannula may be configured with a coil made of a shape memory material, and the coil may be disposed over the outer diameter of the inner layer. The cannula may further have a thermoformed outer layer extending along the length of the cannula, and being disposed over the inner layer and the coil. In certain implementations, the coil is embedded in the outer layer. In further implementations, the shape memory material which the coil comprises is at least one of Nitinol or a copper-aluminum alloy. The outer layer of the cannula comprises an outer material. In certain implementations, the outer material comprises polyurethane. In some implementations, the outer material comprises Texin®. Texin is thermoplastic polyurethane (TPU). In some implementations, the inner material comprises polyurethane. In other implementations, the inner material comprises Texin®. Where polyurethane is used for the inner layer and/or the outer layer, it may comprise polyether or polyester. In certain implementations, the inner and outer materials are the same.

In some implementations, the inner layer extends longitudinally beyond the outer layer at least one of the distal and the proximal ends of the cannula body. These longer portions of the inner layer are referred to as a distal inner projection and a proximal inner projection, respectively. In implementations having a distal inner projection, the addition of a thermoformed outer end reinforcement layer to the end of the outer layer may create a continuous reinforcement profile along the length of the cannula. In certain implementations, at least one of the distal and proximal inner projections has a length of between about 1 centimeter and about 5 centimeters. In other implementations, at least one of the distal and proximal inner projections has a length of between about 2 centimeters and about 4 centimeters. In certain implementations, at least one of the distal and proximal inner projections has a length of about 3 centimeters.

Additionally, the cannula may further comprise a first thermoformed outer end reinforcement layer. In some implementations, the first thermoformed outer end reinforcement layer extends over the outer layer of the cannula at the proximal end of the cannula. In other implementations, the first thermoformed outer end reinforcement layer extends over the proximal portion of the proximal inner layer that is longer than the outer layer so as to create a continuous reinforcement profile along the length of the cannula. The first thermoformed outer end reinforcement layer may comprise a reinforcement material and form a reinforced section between the cannula and the pump housing. The first thermoformed outer end reinforcement layer may be configured to reduce the chance of separation between the pump housing and the cannula due to the forces exerted on the cannula during the percutaneous insertion of the intravascular blood pump system into the body of a patient. When the blood pump assembly is in position within the heart of a patient, the cannula may extend across the aortic valve of the patient such that the distal end of the cannula is disposed within the left ventricle and the proximal end of the cannula is disposed within the aorta.

In certain implementations, the cannula further includes a second thermoformed outer end reinforcement layer. In some implementations, the second thermoformed outer end reinforcement layer is disposed over the outer layer at the distal end of the cannula. In other implementations, the second thermoformed outer end reinforcement layer extends over the distal inner projection so as to create a continuous reinforcement profile along the length of the cannula. In such implementations, the distal thermoformed outer end reinforcement layer comprises the reinforcement material. In some implementations, the distal end of the cannula interfaces with an inflow cage, and the distal thermoformed outer end reinforcement layer forms a second reinforced section of the cannula at the interface between the cannula and the inflow cage. In implementations having a distal thermoformed outer end reinforcement layer, the distal thermoformed outer end reinforcement layer may serve as a strain relief section that reduces the chance of separation between the inflow cage and the cannula due to the forces exerted on the cannula during the percutaneous insertion.

In some implementations, the radial thickness of the reinforcement layer tapers. For example, the proximal thermoformed outer end radial thickness may be tapered so that it reduces in thickness in the distal direction. In other implementations, the radial thickness of the distal thermoformed outer end reinforcement layer may be tapered so that it reduces in thickness in the distal direction. In certain implementations, the radial thickness of both of the thermoformed outer end reinforcement layers may be tapered so that they reduce in thickness in the distal direction. In certain implementations, the radial thickness of at least one of the thermoformed outer end reinforcement layers tapers from about 1-millimeter-thick to a minimized thickness near 0. In other implementations, the radial thickness of at least one of the thermoformed outer end reinforcement layers tapers from about 0.7 millimeters thick to near 0. In further implementations, the radial thickness of at least one of the thermoformed outer end reinforcement layers tapers from about 0.4 millimeters to near 0.

In some implementations, the inner layer comprises an inner material, the outer layer comprises an outer material, and the thermoformed outer end reinforcement layer comprises a reinforcement material. In certain implementations, the inner material and the outer material comprise the same material. In some implementations, at least one of the inner material and the outer material is polyurethane. In further implementations, the inner material is polyester polyurethane. In other implementations, the inner material is polyether urethane. In certain implementations, at least one of the outer material and the reinforcement material is polyether polyurethane. In some implementations, at least one of the inner material and the outer material is Texin®. The polymer may be selected based on its behavior during heat-shrinking. Further, the specific polymer selected for use in the cannula may be chosen for its specific mechanical properties. For example, the chosen polymer may have a rigidity such that when the cannula is subject to stress, the cannula body will bend more readily than the thermoformed outer end reinforcement layer(s).

In some implementations, the reinforced portion of the cannula is between about 0.5 times and 3 times as stiff as the medial portion of the cannula. In other implementations, the reinforced portion of the cannula is between about 1 times and about 2.75 times as stiff as the medial portion of the cannula. In further implementations, the reinforced portion of the cannula is between about 1.5 times and about 2.5 times as stiff as the medial portion of the cannula. In certain implementations, the reinforced portion of the cannula less than 2.5 times as stiff as the medial portion of the cannula. The relative stiffnesses of the reinforced portion of the cannula and the medial portion of the cannula can be adjusted by the incorporation of one or more thermoformed outer end reinforcement layers of varying stiffnesses. Additionally, the relative stiffnesses can be adjusted by the incorporation of materials having varying rigidities encompassed by the below ranges. The relative stiffnesses of the reinforced portion of the cannula and of the medial portion of the cannula can advantageously be selected so as to reduce the likelihood of kinking that would otherwise occur due to a large difference in stiffnesses between the reinforced portion of the cannula and the medial portion of the cannula.

The thermoformed outer end reinforcement layer may comprise a material with a higher stiffness than the materials of the medial portion of the cannula. Further, the geometry of the thermoformed outer end reinforcement layer can be adjusted to attain the desired relative stiffness between the thermoformed outer end reinforcement layer and the medial portion. For example, the thermoformed outer end reinforcement layer may have a radial thickness between about 0 and between about 0.3 mm. In further implementations, the radial thickness of the thermoformed outer end reinforcement layer is between about 0.05 mm and about 0.15 mm. In certain implementations, the radial thickness of the thermoformed outer end reinforcement layer is between about 0.075 mm and about 0.125 mm. In further implementations, the radial thickness of the thermoformed outer end reinforcement layer is less than about 0.1 mm. Additionally, the thermoformed outer end reinforcement layer may have a varying length. In certain implementations, the length of the thermoformed outer end reinforcement layer is between about 1 centimeter and about 3 centimeters. In other implementations, the length of the thermoformed outer end reinforcement layer is about 2 centimeters. In some implementations, the length of the thermoformed outer end reinforcement layer is between about 3 mm and about 9 mm. In certain implementations, the length of the thermoformed outer end reinforcement layer is between about 5 mm and about 7 mm. In other implementations, the length of the thermoformed outer end reinforcement layer is about 6 mm. At least one advantage of the variability of the stiffness of the cannula with the cannula geometry and materials is that the stiffness profile along the length of the cannula can be adjusted. For example, a given procedure may require a cannula of a certain stiffness based on the insertion angle of the procedure. The insertion angle of a procedure may vary based on the patient anatomy and the insertion site. Thus, the geometry and the materials of the cannula may be adjusted to yield a specific stiffness profile along the length of the cannula that would be desirable for a given procedure.

In certain implementations, the inner material has an inner material hardness between about 45D and about 65D. In other implementations, the inner material has an inner material hardness between about 50D and about 60D. In further implementations, the inner material has an inner material hardness of about 55D. In some implementations, the outer material has an outer material hardness between about 75A and about 95A. In other implementations, the outer material has an outer material hardness between about 80A and about 90A. In further implementations, the outer material has an outer material hardness of about 85A. In some implementations, the hardness of the reinforcement material is between about one grade and about 3 grades higher than that of the inner material. In certain implementations, the hardness of the reinforcement material is about 2 grades higher than that of the inner material. In certain implementations, the reinforcement material has a reinforcement hardness between about 45D and about 65D. In other implementations, the reinforcement material has a reinforcement hardness between about 50D and about 60D. In further implementations, the reinforcement material has a reinforcement hardness of about 55D. In certain implementations, the inner hardness and the reinforcement hardness may be equal or approximately equal. The relative hardnesses of the inner material, the outer material, and the reinforcement material may be selected such that the thermoformed outer end reinforcement layers serve as strain relief sections when the cannula is subject to stresses.

In some implementations, the medial portion of the cannula has an outer diameter that is less than the outer diameter of one or both reinforced portions of the cannula. The outer diameter of the medial portion of the cannula may be configured to extend over a range of diameters in order to yield an acceptable stiffness of the cannula body. In some implementations, the outer diameter of the reinforced outer end layer is greater than an average outer diameter of the medial portion of the cannula. In certain implementations, the outer diameter of the medial portion of the cannula is between about 2 Fr and about 7 Fr, and the outer diameter of the reinforced portion of the cannula is between about 3 Fr and about 8 Fr. In other implementations, the outer diameter of the medial portion of the cannula is between about 3 Fr and about 6 Fr, and the outer diameter of the reinforced portion of the cannula is between about 4 Fr and about 7 Fr. In certain implementations, the outer diameter of the medial portion of the cannula is between about 4 Fr and 5 Fr, and the outer diameter of the reinforced portion of the cannula is between about 5 Fr and 6 Fr.

In certain implementations, the medial portion of the cannula is configured to have an inner layer, a coil, and an outer layer, while the reinforced portion of the cannula is an extension of the cannula from the medial portion which further includes a thermoformed outer end reinforcement layer in one or both of the cannula's end regions.

Methods are also contemplated for manufacturing a cannula with an inner layer and reinforced end regions. In an implementation, the cannula is manufactured by thermoforming the inner layer over a mandrel, placing a shape memory coil over the outer diameter of the inner layer, and thermoforming the cannula's outer layer so it extends along the length of the cannula, over the inner layer and the cannula's coil. An outer end reinforcement layer is then thermoformed to extend over the cannula's outer layer at the proximal end of the cannula. The thermoformed outer end reinforcement layer forms a reinforced section of the cannula between the cannula and the pump housing. The thermoformed outer end reinforcement layer is configured to help prevent separation between the pump housing and the cannula during the percutaneous insertion of the intravascular blood pump system into the body of a patient. Additionally, the reinforced section of the cannula is configured to increase the stiffness of the cannula at an interface between the cannula and the pump housing. In some implementations, the reinforced portion of the cannula is between about 1.5 times and 5.5 times as stiff as the medial portion of the cannula. In other implementations, the reinforced portion of the cannula is between about 2 times and about 5 times as stiff as the medial portion of the cannula. In further implementations, the reinforced portion of the cannula is between about 3 times and about 4 times as stiff as the medial portion of the cannula. In certain implementations, the reinforced portion of the cannula is about 3.5 times as stiff as the medial portion of the cannula. In another implementation, the method for manufacturing a cannula for use in a blood pump assembly comprises a cannula that is bonded to a pump housing of the pump assembly and to an inflow cage of the pump assembly, the pump housing being configured to at least partially enclose a rotor. In such implementations, the method further comprises bonding an inflow cage to the distal end of the cannula and bonding the pump housing to the proximal end of the cannula. In further implementations, at least one of bonding the inflow cage to the distal end of the cannula and bonding the pump housing to the proximal end of the cannula comprises applying an epoxy to the components to be bonded and heat-curing the epoxy.

In certain implementations, thermoforming the inner layer involves placing an inner extruded sleeve on a mandrel and placing a first heat shrink tube around the inner extruded sleeve. The heat shrink tube and the inner extruded sleeve are then heated so as to soften the sleeve and to cause the heat shrink tube to apply a compressive force on the sleeve in the direction of the mandrel. The first heat shrink tube is then removed.

In other implementations, thermoforming the outer layer comprises placing an outer extruded sleeve, the outer extruded sleeve comprising the outer material, over the inner layer and the coil, and subsequently placing a second heat shrink tube around the outer extruded sleeve. The heat shrink tube and the outer extruded sleeve are then heated so as to soften the sleeve and to cause the second heat shrink tube to apply a compressive force on the sleeve in the direction of the inner layer and the coil, causing the coil to be embedded in the outer material. The second heat shrink tube is subsequently removed.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, methods, and devices disclosed herein, certain illustrative implementations will be described. Although the implementations and features described herein are specifically described for use in connection with a blood pump assembly, it will be understood that the teaching may be adapted and applied to other pumps and other types of medical devices.

Figure 1:
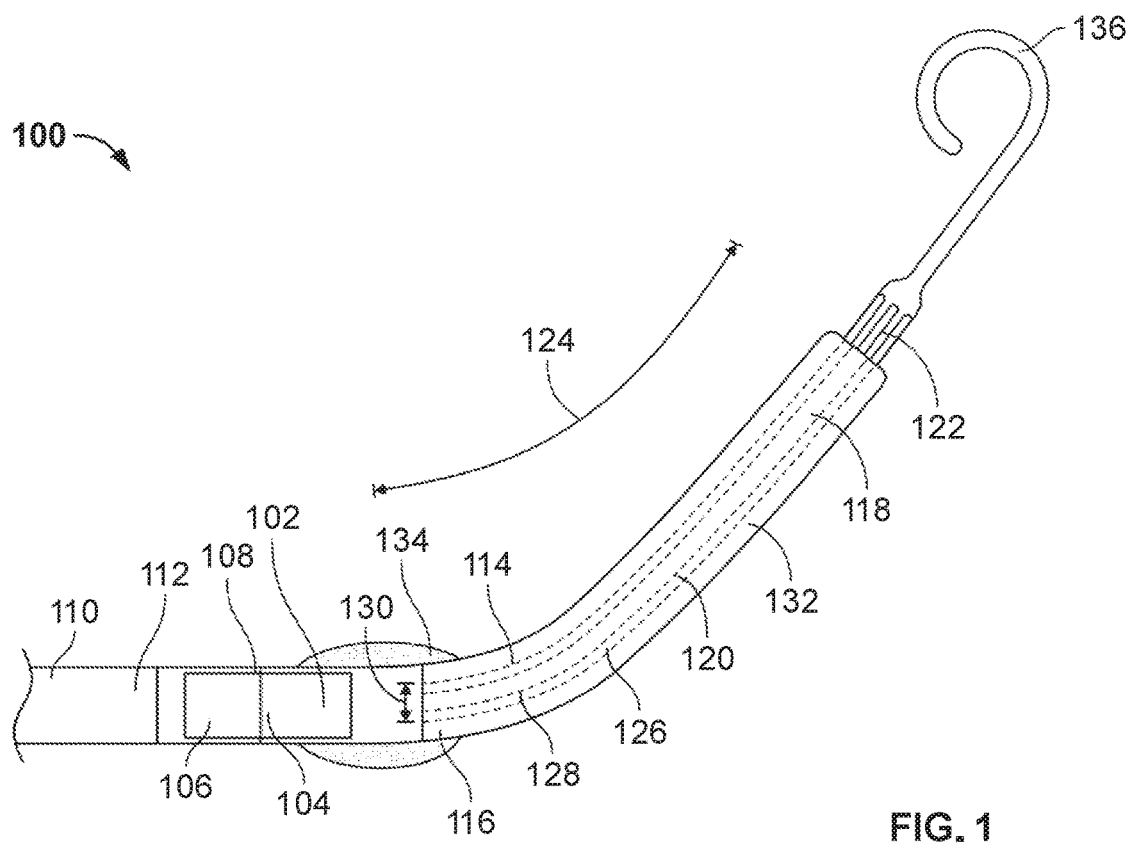
FIG. 1 shows an illustrative blood pump assembly having a thermoformed outer end reinforcement layer at its proximal end in accordance with aspects of the disclosure.

FIG. 1 shows an illustrative blood pump assembly 100 having a pump 102 comprising a motor 106 and a rotor 104, a pump housing 108, a catheter 110 having a distal end 112, a cannula 114 having a proximal end 116, a distal end 118, a medial portion 120, a length 124, a thermoformed inner layer 126, a coil 128, an inner layer outer diameter 130, a thermoformed outer layer 132, a thermoformed outer end reinforcement layer 134, and an atraumatic extension 136. Rotor 104 of pump 102 comprises at least one blade (not shown) for conveying fluid through pump 102. Pump housing 108 surrounds the at least one blade of rotor 104. Proximal end 116 of cannula 114 is coupled to pump housing 108, and distal end 118 of cannula 114 is coupled to a blood inflow cage 122 which itself is coupled to the flexible, atraumatic extension 136. Extension 136 may help to stabilize pump 102 when pump 102 is deployed within the patient by serving as a flow-straightening region. In some implementations, extension 136 is a pigtail.

Cannula 114 may have the same structure as shown below with respect to FIG. 2. In that regard, the cannula 114 of FIG. 1 comprises a thermoformed inner layer 126 extending along length 124 of cannula 114, inner layer 126 comprising an inner material. Additionally, cannula 114 comprises a coil 128 disposed over the thermoformed inner layer 126 and comprising a shape memory material. Cannula 114 further comprises a thermoformed outer layer 132 extending along length 124. The outer layer comprises an outer material. Thermoformed outer end reinforcement layer 134 extends over the outer layer of cannula 114 at proximal end 116 of cannula 114. Thermoformed outer end reinforcement layer 134 comprises a reinforcement material. Further, thermoformed outer end reinforcement layer 134 provides added stability to the joint between cannula 114 and pump housing 108.

In some implementations, thermoformed outer end reinforcement layer 134 is at least two times as stiff as medial portion 120 of cannula 114. In other implementations, thermoformed outer end reinforcement layer 134 is between about 1.5 times and 5.5 times as stiff as medial portion 120 of cannula 114. In other implementations, thermoformed outer end reinforcement layer 134 is between about 2 times and about 5 times as stiff as medial portion 120 of cannula 114. In further implementations, thermoformed outer end reinforcement layer 134 is between about 3 times and about 4 times as stiff as medial portion 120 of cannula 114. In certain implementations, thermoformed outer end reinforcement layer 134 is about 3.5 times as stiff as medial portion 120 of cannula 114.

As discussed previously, in certain implementations, the inner material has a hardness between about 45D and about 65 D. In other implementations, the inner material has a hardness between about 50D and about 60D. In further implementations, the inner material has a hardness of about 55D. In some implementations, the outer material has a hardness between about 75A and about 95A. In other implementations, the outer material has a hardness between about 80A and about 90A. In further implementations, the outer material has a hardness of about 85A. In certain implementations, the reinforcement material has a hardness between about 45D and about 65D. In other implementations, the reinforcement material has a hardness between about 50D and about 60D. In further implementations, the reinforcement material has a hardness of about 55D. In certain implementations, the hardness of the inner material and the reinforcement material are equal or approximately equal.

The relative stiffnesses of the reinforced portion of the cannula and the medial portion of the cannula can be adjusted to yield a desired stiffness profile along the length of the cannula. The relative stiffnesses can be adjusted by the incorporation of one or more thermoformed outer end reinforcement layers of varying stiffnesses. The thermoformed outer end reinforcement layers may comprise a material with a higher stiffness than the medial portion of the cannula. The relative stiffness can be further adjusted by the incorporation of materials having varying rigidities encompassed by the above ranges. Additionally, the geometry of the thermoformed outer end reinforcement layer can be adjusted to attain the desired relative stiffnesses. For example, the thermoformed outer end reinforcement layer 134 may have a radial thickness between about 0.05 mm and about 0.15 mm. In certain implementations, the radial thickness of the thermoformed outer end reinforcement layer 134 is less than about 0.1 mm. Additionally, the thermoformed outer end reinforcement layer 134 may have a varying length. In certain implementations, the length of the thermoformed outer end reinforcement layer 134 is between about 1 centimeter and about 3 centimeters. In other implementations, the length of the thermoformed outer end reinforcement layer 134 is about 2 centimeters. In some implementations, the length of the thermoformed outer end reinforcement layer 134 is between about 3 mm and about 9 mm. In certain implementations, the length of the thermoformed outer end reinforcement layer 134 is between about 5 mm and 7 mm. In other implementations, the length of the thermoformed outer end reinforcement layer 134 is about 6 mm. In general, different procedures requiring different insertion methods and angles may call for cannulas having a specific stiffness profile along the length of the cannula. For example, some femoral insertions of blood pump assemblies into obese patients suffer from kinking because the blood vessel is deeper with respect to the insertion point than in a patient of a lower bodyweight. In such cases, it may be desirable to increase the reinforcement on the distal end and the proximal end of a cannula that is inserted in procedures for obese patients.

Figure 2:
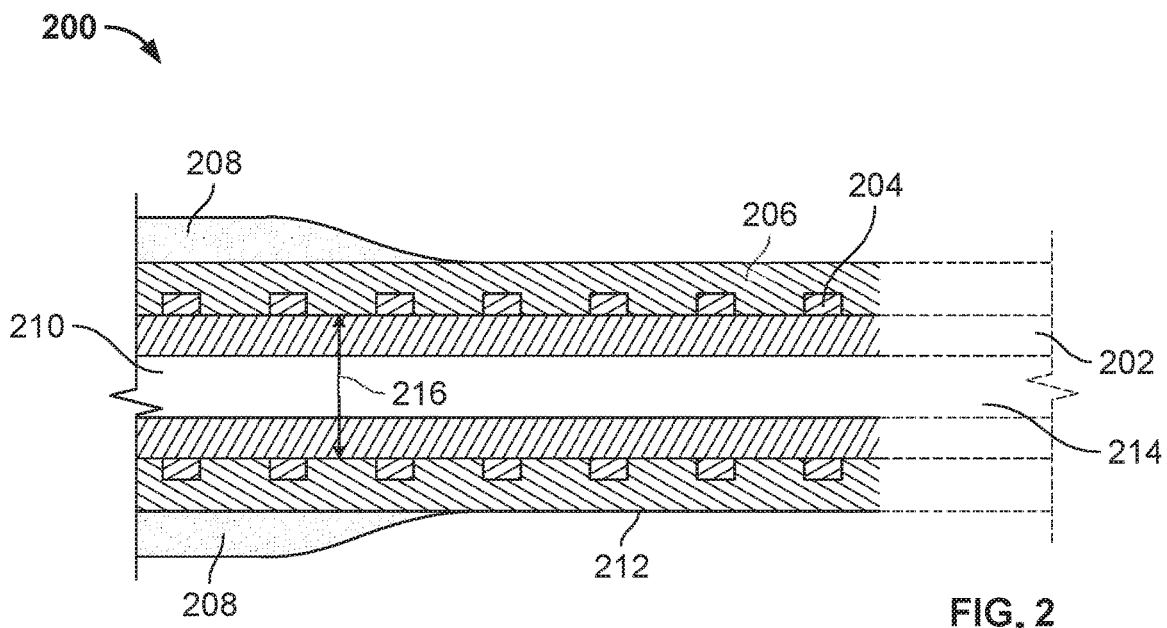
FIG. 2 shows an illustrative cross-section of a cannula for use in a blood pump assembly having a thermoformed outer end reinforcement layer in accordance with aspects of the disclosure.

FIG. 2 shows an illustrative partial longitudinal cross-section of a cannula 200 for use in a blood pump assembly having a thermoformed outer end reinforcement layer, such as the cannula 114 of FIG. 1. Cannula 200 of FIG. 2 has an inner layer 202, a coil 204, an outer layer 206, a thermoformed outer end reinforcement layer 208, a proximal end 210, a medial portion 212, and a distal end 214. Inner layer 202 has outer diameter 216. Inner layer 202 comprises an inner material. Similarly, outer layer 206 comprises an outer material. In some implementations, the inner material is polyurethane. In some implementations, the outer material is polyurethane. In such cases, the polyurethane of the inner and/or outer materials may comprise polyether or polyester. Coil 204 comprises a shape memory material, and coil 204 is disposed over inner layer 202. The shape memory material may be Nitinol or a copper-aluminum alloy. Thermoformed outer end reinforcement layer 208 extends over outer layer 206 at proximal end 210 of cannula 200. Thermoformed outer end reinforcement layer 208 comprises a reinforcement material and forms a reinforced section at or near where cannula 200 is coupled to, for example, a pump housing (e.g., pump housing 108 of FIG. 1).

In some implementations, thermoformed outer end reinforcement layer 208 is between about 1.5 times and 5.5 times as stiff as medial portion 212 of cannula 200. In other implementations, thermoformed outer end reinforcement layer 208 is between about 2 times and 5 times as stiff as medial portion 212 of cannula 200. In further implementations, thermoformed outer end reinforcement layer 208 is between about 3 times and about 4 times as stiff as medial portion 212 of cannula 200. In certain implementations, thermoformed outer end reinforcement layer 208 is about 3.5 times as stiff as medial portion 212 of cannula 200. At least one advantage of the varying relative stiffnesses of thermoformed outer end reinforcement layer 208 and medial portion 212 is that a cannula having a specific rigidity profile can be selected for a procedure depending on the tortuosity of the vasculature that will be traversed by the cannula during the procedure.

The relative stiffnesses of thermoformed outer end reinforcement layer 208 and medial portion 212 of cannula 200 can be adjusted by varying the geometry of one or both of these elements in order to yield a desired stiffness profile along the length of cannula 200. For example, thermoformed outer end reinforcement layer 208 can be made stiffer by increasing the radial thickness of thermoformed outer end reinforcement layer 208. Additionally, medial portion 212 can be made less stiff than thermoformed outer end reinforcement layer 208 by decreasing the radius of medial portion 212. Further, the relative stiffnesses of medial portion 212 and thermoformed outer end reinforcement layer 208 can be adjusted by changing outer diameter 216 of inner layer 202. For example, increasing outer diameter 216 of inner layer 202 while keeping the same thickness of the inner layer 202 and the same outer diameter of outer layer 206 results in a lower stiffness of medial portion 212 as there is less material within medial portion 212 to bend. Conversely, decreasing outer diameter 216 of inner layer 202 while keeping the same thickness of the inner layer 202 and the same outer diameter of outer layer 206 results in a larger stiffness of medial portion 212 as there is a larger amount of material within medial portion 212 to bend. Additionally, the relative stiffnesses between medial portion 212 and thermoformed outer end reinforcement layer 208 can be adjusted by the incorporation of materials having varying stiffnesses. At least one advantage of being able to adjust the relative stiffnesses between medial portion 212 of cannula 200 and thermoformed outer end reinforcement layer 208 is that a desired stiffness profile that is particularly suitable for a given procedure can be implemented along the length of cannula 200.

Figure 3:
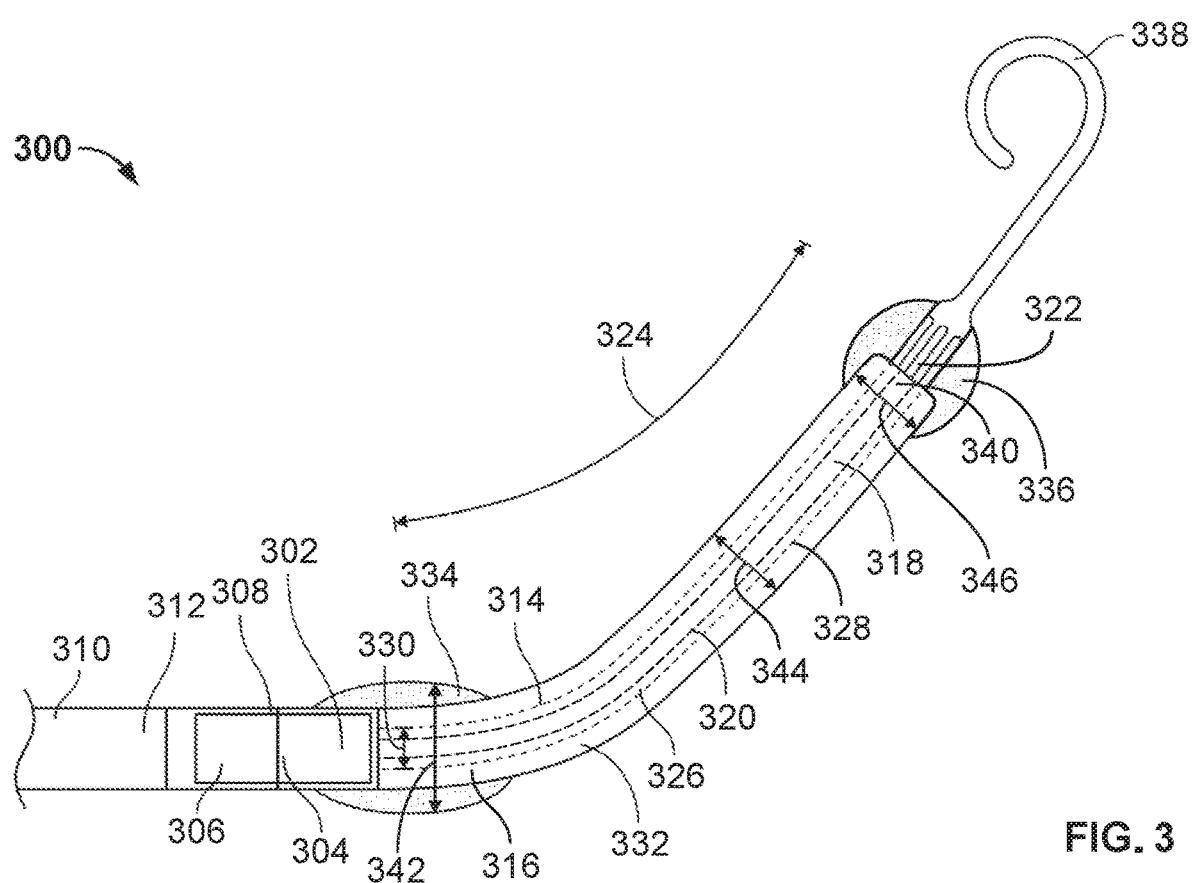
FIG. 3 shows an illustrative blood pump assembly having two thermoformed outer end reinforcement layers in accordance with aspects of the disclosure.

FIG. 3 shows an illustrative blood pump assembly 300 having a pump 302, pump 302 comprising a motor 306 and a rotor 304, a pump housing 308, a catheter 310 having a distal end 312, a cannula 314 having a proximal end 316, a distal end 318, a medial portion 320, a distal opening 340, a length 324, a thermoformed inner layer 326, a coil 328, an inner layer outer diameter 330, a thermoformed outer layer 332, a proximal thermoformed outer end reinforcement layer 334, a distal thermoformed outer end reinforcement layer 336, an atraumatic extension 338, and an inflow cage 322. Similar to thermoformed outer end reinforcement layer 134 of FIG. 1, proximal thermoformed outer end reinforcement layer 334 extends over the outer layer of cannula 314 at proximal end 316 of cannula 314, and comprises a reinforcement material. The proximal thermoformed outer end reinforcement layer 334 may provide added stability to the cannula 314 at or near the interface between cannula 314 and pump housing 308. Likewise, distal thermoformed outer end reinforcement layer 336 extends over the outer layer of cannula 314 at distal end 318 of cannula 314, and comprises a reinforcement material which may be the same or different than the reinforcement material used for proximal thermoformed outer end reinforcement layer 334. The distal thermoformed outer end reinforcement layer 336 may provide added stability to the cannula 314 at or near the interface between cannula 314 and inflow cage 322.

Proximal thermoformed outer end reinforcement layer 334 has outer diameter 342, and medial portion 320 has outer diameter 344. In some implementations, outer diameter 344 of medial portion 320 is less than outer diameter 342 of proximal thermoformed outer end reinforcement layer 334. Similarly, distal thermoformed outer end reinforcement layer 336 has outer diameter 346. In some implementations, outer diameter 344 of medial portion 320 is less than outer diameter 346 of distal thermoformed outer end reinforcement layer 334.

In some implementations, at least one of proximal thermoformed outer end reinforcement layer 334 and distal thermoformed outer end reinforcement layer 336 is between about 1.5 times and 5.5 times as stiff as medial portion 320 of cannula 314. In other implementations, at least one of proximal thermoformed outer end reinforcement layer 334 and distal thermoformed outer end reinforcement layer 336 is between about 2 times and 5 times as stiff as medial portion 320 of cannula 314. In further implementations, at least one of proximal thermoformed outer end reinforcement layer 334 and distal thermoformed outer end reinforcement layer 336 is between about 3 times and 4 times as stiff as medial portion 320 of cannula 314. In certain implementations, at least one of proximal thermoformed outer end reinforcement layer 334 and distal thermoformed outer end reinforcement layer 336 is about 3.5 times as stiff as medial portion 320 of cannula 314. As previously discussed, the relative stiffnesses of the reinforced portion of the cannula and the medial portion of the cannula can be adjusted to yield a desired stiffness profile along the length of the cannula by varying the geometry and the materials of the reinforced and the medial portions of the cannula. As already noted, different procedures requiring different insertion methods and angles may call for cannulas with different stiffness profiles.

Figure 4:
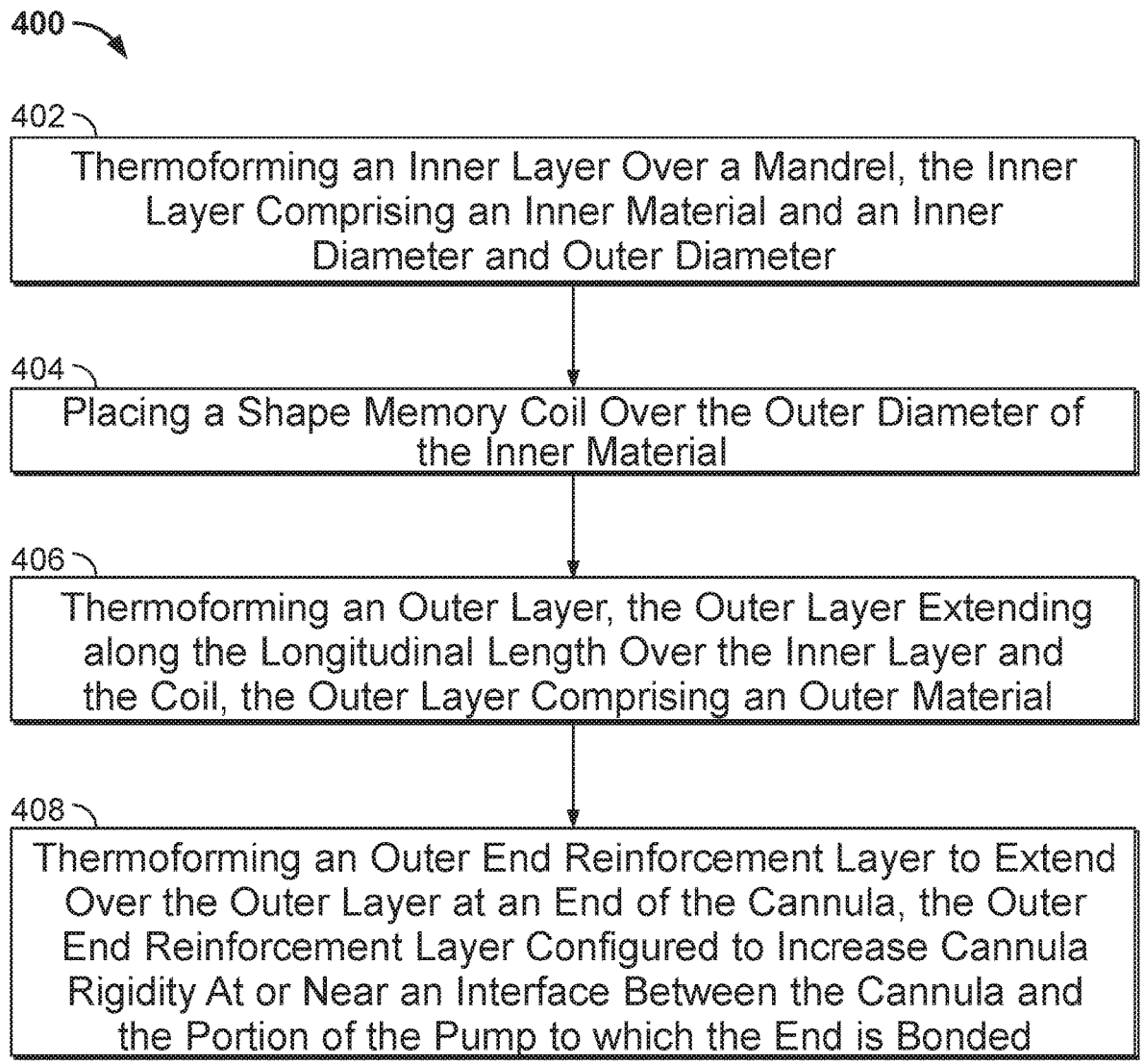
FIG. 4 shows an illustrative method for manufacturing a reinforced cannula in accordance with aspects of the disclosure.

FIG. 4 shows an illustrative method 400 of manufacturing a cannula. The cannula may be, for example, any of the cannulas described above in relation to FIGS. 1-3. Method 400 first comprises step 402, in which an inner layer is thermoformed over a mandrel, and wherein the inner layer comprises an inner material, an inner diameter, and an outer diameter. Step 404 subsequently comprises placing a shape memory coil over the outer diameter of the inner material. Step 406 then comprises thermoforming an outer layer over the coil and the inner layer, wherein the outer layer is configured to extend along the length of the cannula. The outer layer comprises an outer material.

Step 408 comprises thermoforming an outer end reinforcement layer to extend over the outer layer at an end of the cannula. The outer end reinforcement layer comprises a reinforcement material and forms a reinforced section of the cannula. For example, the reinforced material may be applied to the proximal end of the cannula as shown in FIGS. 1 and 2, and be configured to increase the stiffness of the cannula at or near an interface between the cannula and the portion of the pump to which the proximal end of the cannula is bonded (e.g., between the cannula and the pump housing). In such cases, the method may further comprise bonding the thermoformed outer end reinforcement layer to the pump housing of the blood pump assembly. Likewise, the reinforcement material may be applied to the distal end of the cannula as shown in FIG. 3, and be configured to increase the stiffness of the cannula at or near an interface between the cannula and the portion of the pump to which the distal end of the cannula is bonded (e.g., between the cannula and the inflow cage). In such cases, the method may further comprise bonding the thermoformed outer end reinforcement layer to the inflow cage of the blood pump assembly.

In some implementations, the thermoformed outer end reinforcement layer is between about 1.5 times and about 5.5 times as stiff as the medial section of the cannula of the blood pump assembly. In other implementations, the thermoformed outer end reinforcement layer is between about 2 times and about 5 times as stiff as the medial section of the cannula of the blood pump assembly. In certain implementations, the thermoformed outer end reinforcement layer is between about 3 times and about 4 times as stiff as the medial section of the cannula of the blood pump assembly. In further implementations, the thermoformed outer end reinforcement layer is between about 3.5 times as stiff as the medial section of the cannula of the blood pump assembly. The thermoformed outer end reinforcement layer may be bonded to the pump housing or to the inflow cage by the application of an epoxy which is cured.

As previously discussed, the thermoforming of the inner layer comprises placing an inner extruded sleeve, the inner extruded sleeve comprising the inner material, on a mandrel and subsequently placing a first heat shrink tube around the inner extruded sleeve. The heat shrink tube and the inner extruded sleeve are then heated so as to soften the sleeve and to cause the heat shrink tube to apply a compressive force on the sleeve in the direction of the mandrel. The first heat shrink tube is then removed. Similarly, the thermoforming of the outer layer comprises placing an outer extruded sleeve, the outer extruded sleeve comprising the outer material, over the inner layer and the coil, and subsequently placing a second heat shrink tube around the outer extruded sleeve. The heat shrink tube and the outer extruded sleeve are then heated so as to soften the sleeve and to cause the heat shrink tube to apply a compressive force on the sleeve in the direction of the inner layer and the coil, causing the coil to be embedded in the outer material. The second heat shrink tube is subsequently removed.

The foregoing description is merely intended to be illustrative of the principles of the technology. As such, the devices and methods described herein can be practiced by other than the described implementations, which are presented for purposes of illustration and not of limitation.

In addition, the disclosed features may be implemented in any combination or subcombination (including multiple dependent combinations and subcombinations) with one or more other features described herein. The various features described or illustrated above, including any components thereof, may also be combined or integrated into other systems. Moreover, certain features may be omitted or not implemented without departing from the spirit of the technology.

The invention claimed is:

1. An intravascular blood pump system comprising:
a pump having a pump housing and a rotor, the pump being configured to be operated by a motor;
an elongate catheter having a distal end, the distal end coupled to the motor or to the pump housing;
a cannula having a proximal end that interfaces with a distal end of the pump housing, a distal end with at least one distal opening, the cannula having a longitudinal length and comprising:
a thermoformed inner layer extending along the longitudinal length of the cannula, the inner layer comprising an inner material;
a coil having a shape memory material, the coil disposed over an outer diameter of the inner layer;
a thermoformed outer layer extending along the longitudinal length over the inner layer and the coil, the outer layer comprising an outer material; and
a thermoformed first outer end reinforcement layer extending over the distal end of the pump housing and the outer layer at the proximal end of the cannula, the first outer end reinforcement layer comprising a first reinforcement material and forming a first reinforced portion of the cannula,
wherein the first reinforced portion of the cannula is at least two times as stiff as a medial portion, the medial portion being distal of the first reinforced portion of the cannula,
wherein a radial thickness of the thermoformed first outer end reinforcement layer is tapered.

2. The system of claim 1, wherein the first reinforced portion of the cannula is at least four times as stiff as the medial portion of the cannula.

3. The system of claim 1, further comprising a thermoformed second outer end reinforcement layer disposed at the distal end of the cannula, wherein the second outer end reinforcement layer comprises a second reinforcement material and forms a second reinforced portion of the cannula, and wherein the medial portion is proximal of the second reinforcement portion of the cannula.

4. The system of claim 1, wherein the radial thickness of the first outer end reinforcement layer tapers in a distal direction.

5. The system of claim 1, wherein the inner material is polyester polyurethane.

6. The system of claim 1, wherein at least one of the outer material or the first reinforcement material is polyether polyurethane.

7. The system of claim 1, wherein the inner material has a hardness in the range of about 45D-65D.

8. The system of claim 1, wherein the outer material has a hardness in the range of about 75A-95A.

9. The system of claim 1, wherein the first reinforcement material has a hardness in the range of about 55D-75D.

10. The system of claim 1, wherein a hardness of the inner material and a hardness of the first reinforcement material are equal.

11. The system of claim 1, wherein the coil is embedded in the outer layer.

12. The system of claim 1, wherein the shape memory material comprises at least one of Nitinol or a copper-aluminum alloy.

13. The system of claim 1, wherein:
an outer diameter of the medial portion of the cannula is less than an outer diameter of the first reinforced portion of the cannula;
the medial portion of the cannula comprises the inner layer, the coil, and the outer layer; and
the first reinforced portion of the cannula comprises the inner layer, the coil, the outer layer, and the first outer end reinforcement layer.

14. The system of claim 1, wherein the cannula is configured to be positioned in a patient's heart such that it extends across an aortic valve of the patient's heart, with the distal end of the cannula being within a left ventricle of the patient's heart and the proximal end of the cannula being within an aorta of the patient's heart.

15. The system of claim 3, wherein the first reinforcement material is the same as the second reinforcement material.

16. The system of claim 3, wherein the distal end of the cannula interfaces with an inflow cage.

17. The system of claim 3, wherein a radial thickness of the second outer end reinforcement layer tapers in a distal direction.

* * * * *

UNITED STATES PATENT AND TRADEMARK OFFICE
CERTIFICATE OF CORRECTION

| | | |
|---|---|---|
| PATENT NO. | : 12,144,936 B2 | Page 1 of 1 |
| APPLICATION NO. | : 16/912293 | |
| DATED | : November 19, 2024 | |
| INVENTOR(S) | : Zhenghong Tao et al. | |

It is certified that error appears in the above-identified patent and that said Letters Patent is hereby corrected as shown below:

In the Specification

Column 9, Line 42:
Now reads: "65 D."; should read -- 65D. --

Signed and Sealed this
Fourth Day of February, 2025

Coke Morgan Stewart
*Acting Director of the United States Patent and Trademark Office*